United States Patent
Alatainio

(10) Patent No.: US 9,274,083 B2
(45) Date of Patent: Mar. 1, 2016

(54) LEAK DETECTOR

(71) Applicant: Jani Alatainio, Torma (FI)

(72) Inventor: Jani Alatainio, Torma (FI)

(73) Assignee: NWD TECHNOLOGIES OY, Kemi (FI)

( * ) Notice: Subject to any disclaimer, the term of this patent is extended or adjusted under 35 U.S.C. 154(b) by 0 days.

(21) Appl. No.: 14/391,265

(22) PCT Filed: Apr. 16, 2013

(86) PCT No.: PCT/FI2013/050417
§ 371 (c)(1),
(2) Date: Oct. 8, 2014

(87) PCT Pub. No.: WO2013/164517
PCT Pub. Date: Nov. 7, 2013

(65) Prior Publication Data
US 2015/0084614 A1    Mar. 26, 2015

(30) Foreign Application Priority Data
May 2, 2012  (FI) ..................................... 20125479

(51) Int. Cl.
*G01N 27/61* (2006.01)
*G01M 3/16* (2006.01)
*G08B 21/20* (2006.01)

(52) U.S. Cl.
CPC ................. *G01N 27/61* (2013.01); *G01M 3/16* (2013.01); *G08B 21/20* (2013.01)

(58) Field of Classification Search
CPC ........... G01N 27/61; G01M 3/16; G01M 3/18
USPC ....................................................... 324/691
See application file for complete search history.

(56) References Cited

U.S. PATENT DOCUMENTS 2,681,571 A    6/1954   Becker
3,757,982 A *  9/1973   Isenberg et al. .......... 220/560.15
(Continued)

FOREIGN PATENT DOCUMENTS

GB    2218242    11/1989
GB    2442015    3/2008
(Continued)

OTHER PUBLICATIONS

International Search Report dated Jun. 24, 2013, corresponding to PCT/FI2013/050417.
Finnish Search Report dated Nov. 16, 2012, corresponding to the Foreign Priority Application No. 20125479.
Japanese Office Action, dated May 12, 2015, in corresponding Japanese Patent Application No. 2015-509468, with partial English translation.

*Primary Examiner* — Jeff Natalini
(74) *Attorney, Agent, or Firm* — Young & Thompson

(57) ABSTRACT

In a fluid leak detector, a sensor film is utilized, which includes a central support film having on its top surface a first patterned, conductive electrode film and on its bottom surface a second patterned, conductive electrode film. Substantially round openings are patterned in the first conductive electrode film. The diameter of the openings is chosen on the basis of the droplet size ensued from the surface tension of the fluid to be measured, such that the forming drop of fluid fits completely into the opening. In the support film and in the second conductive electrode film, openings have been punched, whose center points are the same as the center points of the openings in the first electrode film. The diameter of the openings made in the support film and in the second electrode film is smaller than the diameter of the openings made in the first electrode film.

15 Claims, 2 Drawing Sheets

(56) References Cited

U.S. PATENT DOCUMENTS

| | | | |
|---|---|---|---|
| 4,677,373 A | 6/1987 | Kobayashi et al. | |
| 4,862,066 A * | 8/1989 | Sato et al. | 324/696 |
| 6,877,359 B2 * | 4/2005 | Huang et al. | 73/40 |
| 7,735,510 B1 | 6/2010 | Carter | |
| 2007/0275296 A1 * | 11/2007 | Ueda et al. | 429/61 |
| 2009/0284382 A1 | 11/2009 | Hill | |
| 2010/0268479 A1 * | 10/2010 | Potyrailo et al. | 702/23 |
| 2010/0302047 A1 | 12/2010 | Wood | |

FOREIGN PATENT DOCUMENTS

| | | |
|---|---|---|
| JP | 54104017 | 8/1979 |
| JP | 360057 | 6/1991 |
| JP | 9243497 | 9/1997 |
| JP | 2002-098610 | 4/2002 |
| WO | 03/046501 | 6/2003 |

* cited by examiner

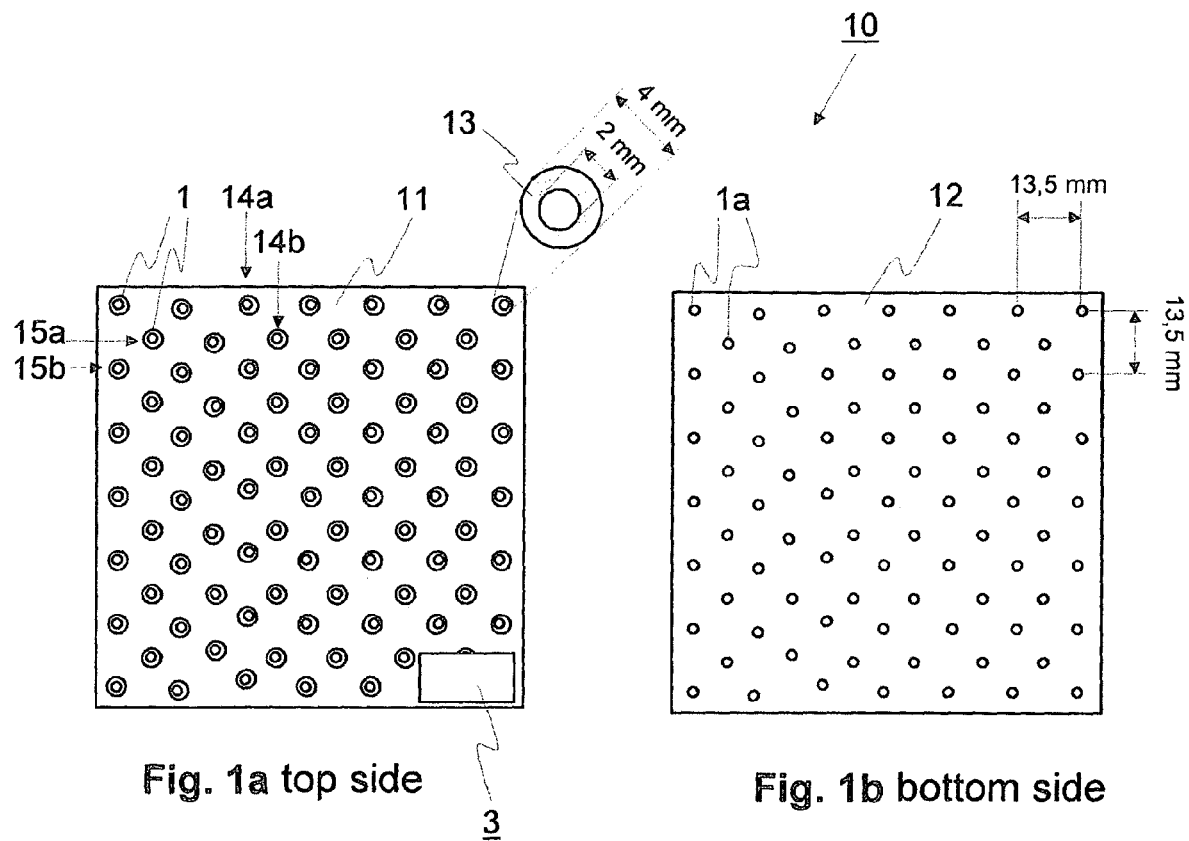
Fig. 1a top side
Fig. 1b bottom side
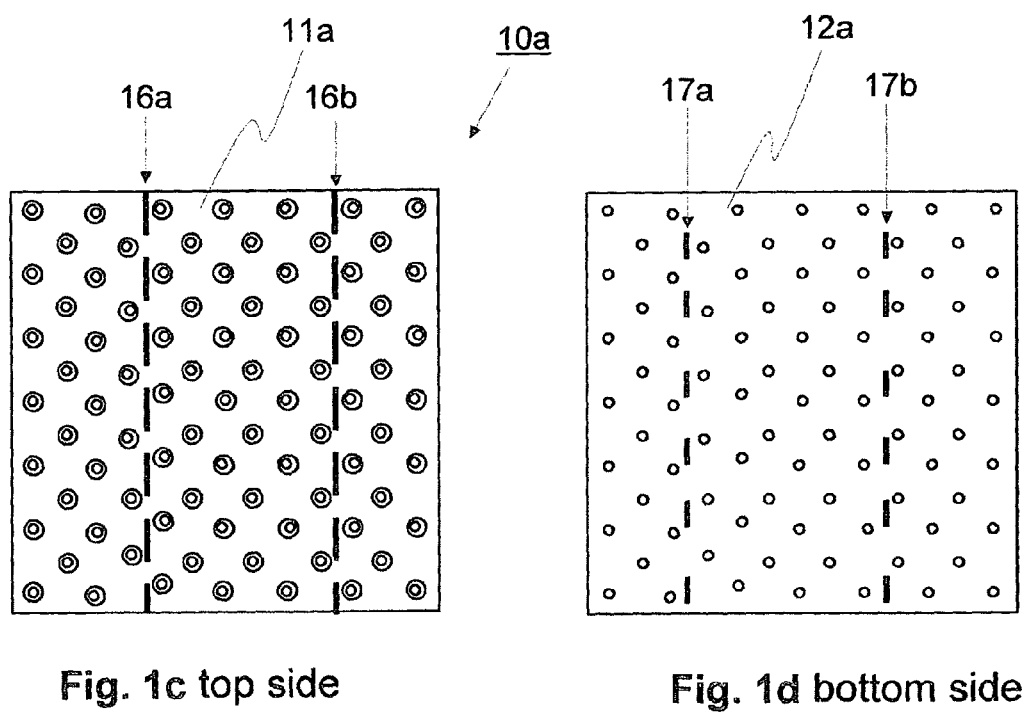
Fig. 1c top side
Fig. 1d bottom side

LEAK DETECTOR

PRIOR ART

Different solutions have been provided for detecting fluid leaks. In U.S. Pat. No. 7,735,510 is provided a trough that is assembled of two components and installed in its place, for example, underneath a sink. On one edge of the trough there is an opening through which the leaking water drains to the front of the cupboards, whereby the hidden water leak can be seen.

In patent JP 9243497 a detector mat is disclosed that consists of crosswise laying conductors on different sides of the support material. If the detector mat becomes wet, the insulation between the crosswise laying conductors becomes conductive. The leakage current formed thereby can be detected and indicated.

In publication US 2009/0284382 a cable-like leak detector is disclosed. The material between the conductors of the cable is insulator when dry, but as it gets wet, it short-circuits the conductors of the cable. The short-circuit current is detected, and it can be indicated either visually or by an alarm signal.

In publication US 2010/0302047 a detector is shown, which consists of two comb-shaped elements. The teeth of the combs are arranged in a staggered manner. If fluid, such as, for example, water, gets in between the teeth of the comb, then between the teeth of two "combs" of the sensor there is electric current which is detected and indicated. This kind of a leak detector is obtainable, for example, at Andel Ltd. This kind of a leak sensor film can be cut only in direction of finger electrodes. Forming of the leak sensor film according to the shape of the object is not possible.

Publication GB 2218242 discloses a solution with two conductive films (at least the "upper one" is perforated), with insulating material in between them. In publication GB 2218242, the insulating layer between the conductive films consists of two separate insulation layers, which at the end step of the manufacturing of the leak detector are joined into an integral structure. One of the insulation layers (films) is joined with the "lower" electrode film and the other one with the "upper" electrode film. Prior to joining the above described two film units (insulation film and electrode film) they are perforated (at least one of them) and cut separately into the shape required by the application. After cutting the electrodes of the described leak detector are placed opposite each other such that the insulation layers are against each other. After this, the structure is "welded" together utilizing the holes in the insulation films. This two-phased cutting arrangement aims at preventing generation of a short circuit between the electrode films in connection with the shape cutting.

Also known are water leak indicators printed on paper. A company producing those is Sensible Solutions Sweden Ab. The leak detector of this company is based on electrodes printed on two sides of a sheet of paper. Because atmospheric humidity has an effect on the base material of the leak detector, the leak detectors need to be replaced at times, if the atmospheric humidity is high. On the other hand, the solution does not allow for the user to modify the detector according to the shape required by the application.

The solutions disclosed in the above-mentioned publications do not enable free shaping of the leak detector into shape of the application.

OBJECTS OF THE INVENTION

It is an object of the invention to provide a new leak detector, the sensor film of which can bee freely shaped, for example by cutting. Openings for pipes or cables going through the film can for example be cut in the sensor film according to the invention without the insulation resistance being reduced below the insulation resistance value predetermined for the leak guard.

SUMMARY OF THE INVENTION

The objects of the invention are achieved by a sensor film with a support film in the middle thereof, and on both sides of the support film conductive electrode films are patterned, both electrode films having opening points aligned with each other. The diameter of the openings of the upper electrode film is large enough, so that a single drop of the fluid to be detected does not fill it. The diameter of the openings of the support film and the lower electrode film is chosen such that the drop of fluid determined by the surface tension of the fluid to be detected penetrates through the opening in spite of the surface tension until the opening of the lower electrode film. Thereby a short circuit is generated between the upper electrode film and the lower electrode film, as a result of which the insulation resistance is reduced below the leak identification limit.

An advantage of the leak guard arrangement according to the invention is that the user can cut from the sensor film a leak sensor in shape of the object to be monitored. A leak sensor film cut into shape can be installed even in very cramped spaces, and, on the other hand, possible leak areas can be extensively covered with a sensor film.

Further, an advantage of the invention is that a sensor film can be manufactured advantageously, for example, as a screen-printed electronics in a roll-to-roll process.

A fluid leak detector according to the invention, comprising detector electronics and its power supply and
a sensor film comprising
  a patterned support film
  a first conductive electrode film formed on a top surface of a support film, the pattern of which electrode film partly covers the top surface of the support film
  a second electrode film formed on a bottom surface of the support film, the pattern of which partly covers the bottom surface of the support film, and the second conductive film being configured for being placed against a surface of an application
  a change of resistance measured between said conductive electrode films is configured to indicate a fluid leak, is characterized in that the pattern of the support film, the pattern of the first conductive electrode film and the pattern of the second conductive electrode film are configured in relation to each other such that the finished sensor film can be cut into a shape required by the application without falling below a resistance value predetermined for the sensor film.

Some advantageous embodiments of the invention are disclosed in the dependent claims.

The basic idea of the invention is the following: In a fluid leak detector according to the invention, a sensor film is utilized, which comprises a central support film and on the top surface thereof a first patterned, conductive electrode film and on the bottom surface of the support film a second patterned, conductive electrode film. The first conductive electrode film is patterned with substantially round openings at equal distances. The size of the openings is chosen on basis of the droplet size ensued the surface tension of the fluid to be measured. The diameter of the opening is large enough for the formed drop of fluid to fit completely in the opening. In the support film and in the second conductive electrode film on its bottom surface, openings have been punched, the centre points of which are the same as the centre points of the openings in the first electrode film. The diameter of the openings made in the support film and in the second electrode film is smaller than the diameter of the openings made in the first electrode film. The diameter of this opening is also chosen on the basis of the surface tension characteristics of the fluid to be measured. The diameter of the opening is chosen such that the drop of fluid of the fluid to be measured is able to penetrate the opening in the support film in spite of the surface tension of the fluid. When the fluid goes through the opening in the support film, then an electrically conductive connection is formed between the first and the second electrode films. Thereby, the insulation resistance between the first and the second electrode films falls below the predetermined threshold value.

BRIEF DESCRIPTION OF THE DRAWINGS

This change of the insulation resistance due to fluid leak is detected by the electronic unit of the fluid leak detector.

In the following, the invention will be described in detail. In the description, reference is made to the enclosed drawings, in which FIG. 1a shows by way of example the upper side of the sensor film according to the first embodiment of the invention, FIG. 1b shows by way of example the bottom side of the sensor film according to the first embodiment of the invention, FIG. 1c shows by way of example the upper side of the sensor film according to the second embodiment of the invention, FIG. 1d shows by way of example the bottom side of the sensor film according to the second embodiment of the invention.

DETAILED DESCRIPTION OF THE PREFERRED EMBODIMENTS

Figure 2:
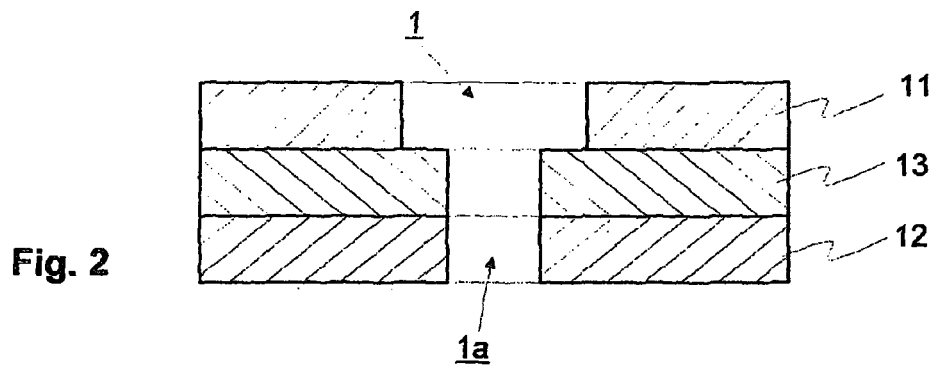
FIG. 2 shows by way of example an opening belonging to the sensor film according to the invention.

The embodiments in the following description are given as examples only, and someone skilled in the art may realize the basic idea of the invention also in some other way than what is described in the description. Though the description may refer to a certain embodiment or embodiments in several places, this does not mean that the reference would be directed towards only one described embodiment or that the described characteristic would be usable only in one described embodiment. The individual characteristics of two or more embodiments may be combined and new embodiments of the invention may thus be provided.

FIGS. 1a and 1b show the sensor film 10 of the first embodiment of the leak detector according to the invention. In this embodiment, the sensor film 10 consists of three successive material layers. The material layer in the middle, the support layer 13, consists advantageously of polyethylene terephthalate (PET). Its thickness can advantageously be chosen according to the application. The thickness can be for example 30-60 μm.

FIG. 1a shows a sensor film 10 according to the first embodiment of the invention in a top view. In this embodiment, on the top surface of the support film 13 an aluminium film is laminated. Its thickness can advantageously be chosen according to the application. The thickness of the aluminium film can be for example 9-36 μm.

After the aluminium film has been laminated onto the support film 13, openings 1 have been etched in the aluminium film at regular distances both in horizontal and vertical directions. Openings 1 made by etching advantageously form columns 14a and 14b and rows 15a and 15b perpendicular to each other in the aluminium film. The distance of adjacent openings 1 from each other in the same row or column can advantageously be in the range of 10-15 mm. Advantageously, the rows of openings and the columns of openings are arranged such that the openings of two adjacent columns 14a and 14b are not aligned in the same row, for example rows 15a and 15b. As all openings are etched in the aluminium film, the first conductive electrode film 11 is successfully formed.

In an advantageous embodiment of the invention, the diameter of the etched openings in the first electrode film 11 is in the order of 4 mm. In this embodiment, in the middle of the etched openings 1, in the next step openings are punched, the diameter of which is in the range of 2 mm. The punched openings extend also through the aluminium film laminated underneath the support film 13 such that their diameter remains the same.

When punching the first electrode film 11 advantageously mechanically with a punching tool, there is a risk of generating a short circuit between the electrode films 11 and 12 on the top and bottom surfaces of the support film 13. This is advantageously prevented by etching openings in the first electrode film 11, the diameter of which is substantially larger than the diameter of the opening made by punching in the support film 13. An opening of corresponding size is needed in the second electrode film 12 on the bottom surface of the support film 13 in order to prevent failure alarms caused by a water layer possibly compressing from the atmospheric humidity on the surface of the second electrode film on the side of the support film.

FIG. 1a further shows an electronic circuit 3 advantageously belonging to the leak detector. The electronic circuit may be an electronic device made of separate components that is advantageously connected to the sensor film 10 according to the invention. Connection of the device can be performed either with separate conductors or by soldering the device into the connection points in the sensor film 10.

In an advantageous embodiment of the invention, at least part of the components of the electronic detector 3 is realized onto the surface of the sensor film 10 by a printing or screen-printing method.

In an advantageous embodiment of the invention, the electronic detector 3 is connected to the sensor film 10 by a separate cable. The conductors of the cable are connected to the electrode films 11 and 12 of the sensor film 10 advantageously by anisotropic glue in the application of the fluid leak sensor. The cable length is advantageously around 1 m.

FIG. 1b shows a sensor film 10 according to the first embodiment of the invention in a view from underneath. Openings of the second electrode film 12 on the bottom surface of the sensor film 10 are advantageously punched from the centre points of the openings 1 of the first electrode film on the top surface of the sensor film 10.

FIG. 1c shows a sensor film 10a according to the second embodiment of the invention in a top view. In this embodiment, on the top surface of the support film 13 an aluminium film is laminated, like in the first embodiment. Its thickness can advantageously be chosen according to the application. The thickness of the aluminium film can be for example 9-36 μm.

After the aluminium film has been laminated onto the support film 13, openings 1 have been etched in the aluminium film, like in the first embodiment. In this embodiment, in addition to the openings, rectangular cutting lines 16a and 16b are etched on the top surface of the sensor film 11a. In these cutting lines the aluminium is removed from the top surface of the support film 13.

FIG. 1d shows respectively a sensor film 10a according to the second embodiment of the invention in a view from underneath. In this embodiment, on the bottom surface of the support film 13 an aluminium film is laminated, like in the first embodiment. Its thickness can advantageously be chosen according to the application. The thickness of the aluminium film can be for example 9-36 μm. In this embodiment, also rectangular cutting lines 17a and 17b are etched on the bottom surface of the sensor film 12a. In these cutting lines the aluminium is removed from the bottom surface of the support film 13.

The cutting lines 16a/16b and 17a/17b shown in FIGS. 1c and 1d are aligned in relation to each other such that by cutting along these cutting lines one or the other surface of the support film respectively is missing the aluminium layer. Thereby, likelihood of a short circuit possibly generated in cutting is minimized.

FIG. 2 shows by way of example the geometric structure of the openings 1 in the sensor film according to the invention. The diameter of the opening made in the first electrode film 11 is substantially larger than the hole penetrating the support film 13 and the second electrode film 12. Thereby, the drop of fluid is able to form an electrically conductive path between the metal films 11 and 12.

If, for example, the diameter of the hole in the first electrode film is 4 mm and the thickness of the support film (PET) is 36 μm, and the diameter of hole of the support film 13 and the second electrode film is 2 mm, and there is deionised water in one hole, a conductive path is created between the first and the second electrode films, the resistance of which being in the range of 10-20 MΩ). Because deionised water does not include ions, its conductivity is lower than for example that of tap water. Thus, it is possible to design the leak detector to be so sensitive that it senses the deionised water in the hole and thus also tap water and, for example, water including detergent.

Figure 3:
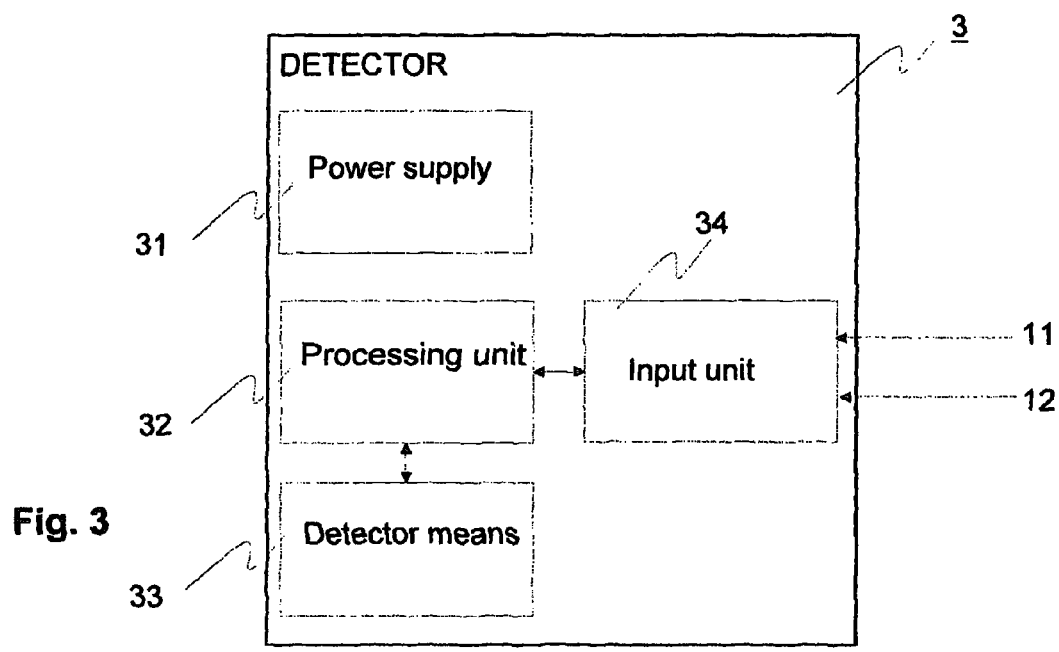
FIG. 3 shows by way of example an electronic unit of the leak sensor according to the invention.

FIG. 3 shows an exemplary electronic detector 3 of a leak detector. The electronic detector 3 may advantageously be attached to the sensor film 10.

In another advantageous embodiment, the electronic detector 3 is a separate electronic unit of its own, connected with a cable to the electrode films 11 and 12 of the sensor film 10.

In a third advantageous embodiment, the two electrode films of the sensor film 10 are utilized as conductors of the connecting cable. In this embodiment, a part of the sensor film is cut in a way that enables voltage supply to the electronic detector 3 from an external voltage source via electrode films 11 and 12.

The detector 3 according to FIG. 3 advantageously comprises a suitable processing unit 32 or a programmable logic. Processing unit 32 is configured to determine and indicate insulation resistance between the first and the second electrode films. If a predetermined insulation resistance value is passed underneath, the detector 3 is configured to detect the fluid leak. Detection of a fluid leak is accomplished by detecting means 33. Detecting means may comprise indicator lights, such as LEDs of different colours and/or a buzzer.

As a power supply 31 of the electronic detector 3 serves a battery or an accumulator, for example a CR2032 3V battery. A full battery lasts for 19 months in monitoring mode, 0.4 months in alarm mode and 1.2 months in low battery mode. In alarm mode the resistance of the sensor film is advantageously measured once in a second.

For example, the following function signals can be programmed in the electronic detector 3 according to the invention:

detector in operation; green LED blinks once in 10 seconds
detector detects fluid; red LED blinks once in a second and/or a sound signal (3 beeps) is given once in 5 seconds
low battery (voltage of the battery lower than 2.5 V); a sound signal once in 10 minutes.

In a fourth advantageous embodiment the processing unit 32 of the circuit board of the detector 3 further comprises opto-isolated open-collector output means, from where a leak alarm can be transmitted to an external alarm arrangement.

In a fifth advantageous embodiment a 24 V/3.3 V direct voltage converter is advantageously installed on the circuit board of the detector 3, by means of which converter the operating voltage utilized in the leak detector can be supplied from an external 9-24V direct voltage source to the detector circuit 3 of the leak detector. Advantageously, the direct voltage converter further comprises a protective insulation of class II, whereby the external voltage supply does not involve danger for the user in any situation.

In a sixth advantageous embodiment mains voltage is utilized as the power supply for the detector 3. Mains voltage is converted to advantageously 5 volt direct voltage by a separate transformer/charging device. The direct voltage is advantageously supplied to the power supply part 31 of the detector 3 via a USB port (Universal Serial Port) integrated in the detector 3. In this embodiment, the detector 3 is advantageously connected to the sensor film 10 with a cable. The detector 3 can be attached for example with an adhesive label on a suitable wall surface at the site of measurement.

In addition to or in place of a light alarm also a buzzer can be utilized as alarm means. The buzzer can be a part of the detector 3, or the buzzer is a part of the above-described charging device.

In an advantageous embodiment, the detector 3 further comprises means for establishing a wireless radio link to the receiver in a property. The receiver is advantageously connected to an electric intelligent system used in property control.

Figure 4:
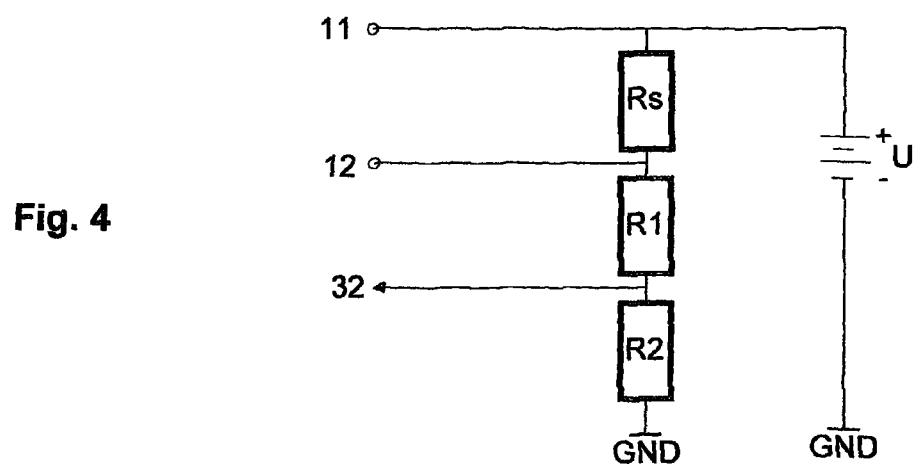
FIG. 4 shows by way of example the connection between the sensor film and the electronic unit.

FIG. 4 shows an example of the connection of the first and the second electrode films of the sensor film 10 with the electronic detector 3. The positive pole of the battery, i.e. voltage +U, is connected to the first electrode film 11. The insulation resistance between the first 11 and the second 12 electrode films is indicated by resistor Rs. Advantageously, it is more than 50 MΩ.

The second electrode film 12 of the sensor film 10 is connected to the positive pole of the resistor R1 belonging to the voltage divider R1 and R2. By the relation of the resistance values R1 and R2 of the voltage divider a threshold value is determined, which causes a leak alarm. In one case, the total resistance of resistors R1 and R2 is advantageously in the range of 10 MΩ. The voltage monitored in leak detection is connected to the input of an A/D converter included in the processing means 32 of the electronic part 3 of the leak detector at the connecting point of resistors R1 and R2. It is assumed, that there is scarcely any current coming to the input of the analog-to-digital converter, whereby the voltage at its input can be calculated from the equation:

$$U_{ADC} = \frac{R2}{Rs + R1 + R2} U$$

When the sensor film 10 according to the invention is dry, its resistance is infinite, and thereby the voltage to be monitored is $U_{ADC}=0$ V. With suitable values of the resistors R1 and R2 the detector unit 3 can be programmed such that the alarm is activated for example when $U_{ADC}$ is above 0.5 V. This corresponds to value of an insulation resistance 38 MΩ in a situation where the original insulation resistance between the electrode films of the leak detector was above 50 MΩ.

Above, a leak sensor according to the invention is described, the electrode films of which are realized by laminating an aluminium film on both sides of the plastic support film.

It is obvious for someone skilled in the art, that the electrode films can be manufactured also by other known manufacturing methods. The electrode films can be manufactured on a support film for example by a printing or screen-printing method (so called printed electronics). In an advantageous embodiment of the invention the electrode of the top surface is screen-printed or printed from carbon paste on the top surface of the support film. The sensitivity of the leak detector can further be adjusted by adding organic paste material to the carbon paste. By a sensitively-adjusted leak detector for example also a humidity damage generated by condensation can be indicated.

Further, it is obvious for someone skilled in the art, that the holes penetrating the support film of the leak detector according to the invention can also be manufactured in other ways than by punching. A possibility is to make the holes by a laser beam.

Naturally, as a support film any film can be used, the insulation resistance of which is tens of megaohms. These films may include different plastic films, films made of organic material or special papers.

With a leak detector according to the invention advantageously a water leak, oil leak, alcohol leak, coolant leak or medicine leak can be detected.

Above, some advantageous embodiments of the leak detector according to the invention have been described. The invention is not limited to the solutions described above, but the inventive idea can be applied in numerous ways within the scope of the claims.

The invention claimed is:

1. A fluid leak detector, comprising:
   detector electronics connected to a power supply; and
   a sensor film connected to the detector electronics, comprising
      a patterned support film,
      a first conductive electrode film formed on a top surface of the patterned support film, a pattern of the first conductive electrode film partly covering the top surface of the patterned support film, and
      a second conductive electrode film formed on a bottom surface of the patterned support film, a pattern of the second conductive electrode film partly covering the bottom surface of the patterned support film, and the second conductive electrode film being configured to be placed against a surface of a mounting place,
      a change of resistance measured between said first and second conductive electrode films being indicative of a fluid leak,
   wherein the pattern of the first patterned conductive electrode film comprises first openings, a diameter of said first openings being larger than that of a drop of fluid,
   wherein the pattern of the second patterned electrode comprises second openings, a diameter of said second openings being approximately that of the drop of fluid,
   wherein said second openings of the second patterned conductive electrode film are aligned with round openings extending through the patterned support film,
   wherein said first openings of the first patterned conductive electrode film and said second openings of the second patterned conductive electrode film are positioned in relation to each other such that pairs of first and second openings, positioned opposite one another on opposite sides of the patterned support film, have common center points, and
   wherein the pattern of the patterned support film, the pattern of the first patterned conductive electrode film, and the pattern of the second patterned conductive electrode film are arranged in relation to each other such that the sensor film can be cut into a shape required by the mounting place without a resistance value of the sensor film falling below a predetermined resistance value for the sensor film.

2. The fluid leak detector according to the claim 1,
   wherein the patterned support film is made of polyethylene terephthalate, and
   wherein the first conductive electrode film and the second conductive electrode film are aluminium films laminated into the polyethylene terephthalate film.

3. The fluid leak detector according to the claim 2,
   wherein the thickness of the polyethylene terephthalate film is 30-60 µm, and
   wherein the thickness of the aluminium films is 9-36 µm.

4. The fluid leak detector according to the claim 1,
   wherein the diameter of said first openings of the first conductive electrode film is approximately 4 mm, and
   wherein the diameter of said second openings of the second conductive electrode film is approximately 2 mm.

5. The fluid leak detector according to claim 4, wherein a drop of fluid on the first conductive electrode film causes an insulation resistance between the first conductive electrode film and the second conductive electrode film to fall below 38 MΩ, and the detector electronics of the leak detector are configured to indicate a fall of said insulation resistance below 38 MΩ.

6. The fluid leak detector according to claim 1, wherein the patterned support film is made of a material having a resistance that diminishes under the influence of fluid.

7. The fluid leak detector according to claim 6, wherein the first conductive electrode film and the second conductive electrode film are patterned by a printing or screen-printing manufacturing method.

8. The fluid leak detector according to claim 7,
   wherein said second openings of the second conductive electrode film extend through the patterned support film into corresponding first openings of the first conductive electrode film.

9. The fluid leak detector according to claim 8, wherein a drop of fluid on the first conductive electrode film causes an insulation resistance of the patterned support film to fall below 38 MΩ, and the detector electronics of the leak detector are configured to indicate a fall of said insulation resistance below 38 MΩ.

10. The fluid leak detector according to claim 9, wherein at least a portion of electric circuit elements of the detector electronics is printed or screen-printed electronics.

11. The fluid leak detector according to claim 10, wherein an input unit of the detector electronics is connected either directly to the first and second conductive electrode films, or the input unit is connected by a cable to the first and second conductive electrode films.

12. The fluid leak detector according to claim 6, wherein at least the first conductive electrode film is made of conductive carbon paste.

13. The fluid leak detector according to claim 12,
said second openings of the second conductive electrode film extend through the patterned support film into said first openings of the first electrode film having common centre points with said second openings of the second conductive electrode film.

14. The fluid leak detector according to claim 1, wherein, the diameter of said first openings is larger than that of a water drop, and the diameter of said second openings is approximately that of the water drop.

15. The fluid leak detector according to claim 1,
wherein the diameter of said first openings is configured to be larger than a droplet size of oil, droplet size of alcohol, droplet size of coolant or droplet size of pharmaceutical fluid, and
wherein the diameter of said second openings is the droplet size of oil, droplet size of alcohol, droplet size of coolant or droplet size of pharmaceutical fluid.

\* \* \* \* \*